United States Patent
Abboud et al.

(10) Patent No.: US 9,027,389 B2
(45) Date of Patent: May 12, 2015

(54) FLUID CONTROL SYSTEM FOR A MEDICAL DEVICE

(75) Inventors: Marwan Abboud, Pierrefonds (CA); Rachid Mahrouche, Lasalle (CA); Teresa Ann Mihalik, Montreal (CA); Chadi Harmouche, St-Laurent (CA); Jean-Luc Pageard, Montreal (CA); John W. Lehmann, Wayland, MA (US)

(73) Assignee: Medtronic CryoCath LP, Toronto, Ontario (CA)

( * ) Notice: Subject to any disclaimer, the term of this patent is extended or adjusted under 35 U.S.C. 154(b) by 333 days.

(21) Appl. No.: 13/526,620

(22) Filed: Jun. 19, 2012

(65) Prior Publication Data

US 2012/0271291 A1 Oct. 25, 2012

Related U.S. Application Data

(60) Continuation of application No. 12/125,533, filed on May 22, 2008, now Pat. No. 8,225,643, which is a division of application No. 11/074,293, filed on Mar. 7, 2005, now Pat. No. 8,206,345.

(51) Int. Cl.
| | |
|---|---|
| *A61B 18/02* | (2006.01) |
| *G01M 3/28* | (2006.01) |
| *A61B 17/00* | (2006.01) |
| *A61B 18/00* | (2006.01) |

(52) U.S. Cl.
CPC ............. *A61B 18/02* (2013.01); *G01M 3/2846* (2013.01); *A61B 2017/00084* (2013.01); *A61B 2018/0022* (2013.01); *A61B 2018/0212* (2013.01); *A61B 2018/0262* (2013.01)

(58) Field of Classification Search
CPC .................... A61B 18/02; A61B 2017/00084; A61B 2018/0212; A61B 2018/0262; A61B 2018/0022; G01M 3/26; G01M 3/2846
USPC ................... 604/96.01, 99.03, 99.04, 101.01; 606/21; 73/40, 40.5 R
See application file for complete search history.

(56) References Cited

U.S. PATENT DOCUMENTS

| | | | |
|---|---|---|---|
| 5,021,046 | A | 6/1991 | Wallace |
| 5,171,299 | A | 12/1992 | Heitzmann et al. |

(Continued)

FOREIGN PATENT DOCUMENTS

| | | | |
|---|---|---|---|
| EP | 1357847 B1 | 8/2002 | |
| EP | 1389477 A1 | 2/2004 | |

(Continued)

*Primary Examiner* — Daniel S Larkin
(74) *Attorney, Agent, or Firm* — Christopher & Weisberg, P.A.

(57) ABSTRACT

The present invention provides a medical device having an elongate body with both a proximal end and a distal end, wherein the elongate body defines an intake lumen and an exhaust lumen. The medical device also has a first pliable element defining a cooling chamber disposed at a point along the elongate body, with the cooling chamber being in fluid communication with the intake lumen and the exhaust lumen. A second pliable element is provided which at least partially encloses the first pliable element, thereby defining a junction between the first and second pliable element. A check valve is included which is in fluid communication with the junction between the first pliable element and second pliable element, the valve further being in fluid communication with the exhaust lumen. Additionally, the medical device may include sensors or other monitoring means in fluid communication with the junction and the cooling chamber.

8 Claims, 4 Drawing Sheets

(56) References Cited

U.S. PATENT DOCUMENTS

| | | |
|---|---|---|
| 5,281,215 A | 1/1994 | Milder |
| 5,368,565 A | 11/1994 | DeLong |
| 5,403,309 A | 4/1995 | Coleman et al. |
| 5,417,689 A | 5/1995 | Fine |
| 5,429,606 A | 7/1995 | Robinson et al. |
| 5,545,133 A | 8/1996 | Burns et al. |
| 5,728,064 A | 3/1998 | Burns et al. |
| 5,868,735 A | 2/1999 | Lafontaine |
| 5,946,920 A | 9/1999 | Clarke |
| 5,964,778 A | 10/1999 | Fugoso et al. |
| 5,980,486 A | 11/1999 | Enger |
| 5,992,158 A | 11/1999 | Goddard et al. |
| 6,007,571 A | 12/1999 | Neilson et al. |
| 6,036,697 A | 3/2000 | DiCaprio |
| 6,179,827 B1 | 1/2001 | Davis et al. |
| 6,355,029 B1 | 3/2002 | Joye et al. |
| 6,440,126 B1 | 8/2002 | Abboud et al. |
| 6,468,268 B1 | 10/2002 | Abboud et al. |
| 6,471,694 B1 | 10/2002 | Kudaravalli et al. |
| 6,514,245 B1 | 2/2003 | Williams et al. |
| 6,575,966 B2 | 6/2003 | Lane et al. |
| 6,648,878 B2 | 11/2003 | Lafontaine |
| 6,648,879 B2 | 11/2003 | Joye et al. |
| 6,796,972 B1 | 9/2004 | Simofsky et al. |
| 6,875,209 B2 | 4/2005 | Zvuloni et al. |
| 6,989,009 B2 | 1/2006 | Lafontaine |
| 2004/0243119 A1 | 12/2004 | Lane et al. |
| 2005/0215989 A1* | 9/2005 | Abboud et al. .......... 606/21 |
| 2005/0228367 A1 | 10/2005 | Abboud et al. |

FOREIGN PATENT DOCUMENTS

| | | |
|---|---|---|
| WO | 0042931 A1 | 7/2000 |
| WO | 02058576 A1 | 8/2002 |
| WO | 03026719 A2 | 4/2003 |
| WO | 2005038357 A2 | 4/2005 |

* cited by examiner

FLUID CONTROL SYSTEM FOR A MEDICAL DEVICE

CROSS-REFERENCE TO RELATED APPLICATION

This application is a continuation of U.S. application Ser. No. 12/125,533, filed May 22, 2008, now U.S. Pat. No. 8,225,643, entitled FLUID CONTROL SYSTEM FOR A MEDICAL DEVICE, which application is a divisional of application Ser. No. 11/074,293, filed on Mar. 7, 2005, now U.S. Pat. No. 8,206,345, entitled FLUID CONTROL SYSTEM FOR A MEDICAL DEVICE, the entirety of which is incorporated herein by reference.

STATEMENT REGARDING FEDERALLY SPONSORED RESEARCH OR DEVELOPMENT n/a

FIELD OF THE INVENTION

The present invention relates to catheters.

BACKGROUND OF THE INVENTION

Catheter based devices are employed in various medical and surgical applications as they are relatively non-invasive and allow for precise treatment of localized tissues that are otherwise inaccessible. Catheters may be easily inserted and navigated through the blood vessels and arteries, allowing non-invasive access to areas of the body with relatively little trauma. A particular application for a catheter-based system is tissue ablation, which is typically achieved by cooling a portion of the catheter to a very low temperature through the use of a cryogenic fluid flowing through the catheter, and subsequently ablating the target tissue through thermal transfer between the catheter and the tissue.

In order to achieve a temperature sufficient to ablate the target tissue, the fluid flowing through the catheter may be highly pressurized. Should any portion of the catheter rupture or develop a fluid leak, the pressurized fluid could disperse into the patient's tissue, potentially causing a life threatening embolus to form. While an outer covering or additional layer of material may be employed to structurally reinforce portions of the catheter to prevent or reduce the likelihood of a fluid leak, a physician performing an ablative procedure may be unaware that a breach or structural failure of a catheter has occurred.

Moreover, an outer layer or covering may be vacuum sealed around the cooling chamber, which may require a vacuum source and/or coupling in addition to the vacuum source and/or coupling attached to a coolant return path providing circulation through the catheter. Having multiple vacuum connections and sources requires additional connectors and flow paths which can complicate the overall catheter and increase the cost of manufacture and implementation.

As such, it would be beneficial to provide a catheter that has the capability to provide substantially instantaneous leak detection while reducing the complexity of the catheter's flow paths and connections.

SUMMARY OF THE INVENTION

The present invention advantageously provides a fluid control system for a medical device. More specifically, the present invention provides a medical device having an elongate body defining both an intake lumen and an exhaust lumen. A first pliable element is included which defines a cooling chamber disposed along the elongate body, where the cooling chamber is in fluid communication with both the intake and exhaust lumens. The present invention further provides a second pliable element which at least partially encloses the first pliable element, and defines a junction between the first and second pliable elements. A check valve is provided in fluid communication with both the junction as well as the exhaust lumen, such that in the event of a leak in the first pliable element, the check valve opens and allows coolant to flow through the junction between the pliable elements and into the exhaust lumen.

In addition, pressure sensors and leak detection elements, may be included for monitoring the conditions within the cooling chamber and junction between the two pliable elements may be included. The sensors can be used to trigger a shut down of the medical device in the event fluid flow exceeds predetermined operating ranges.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
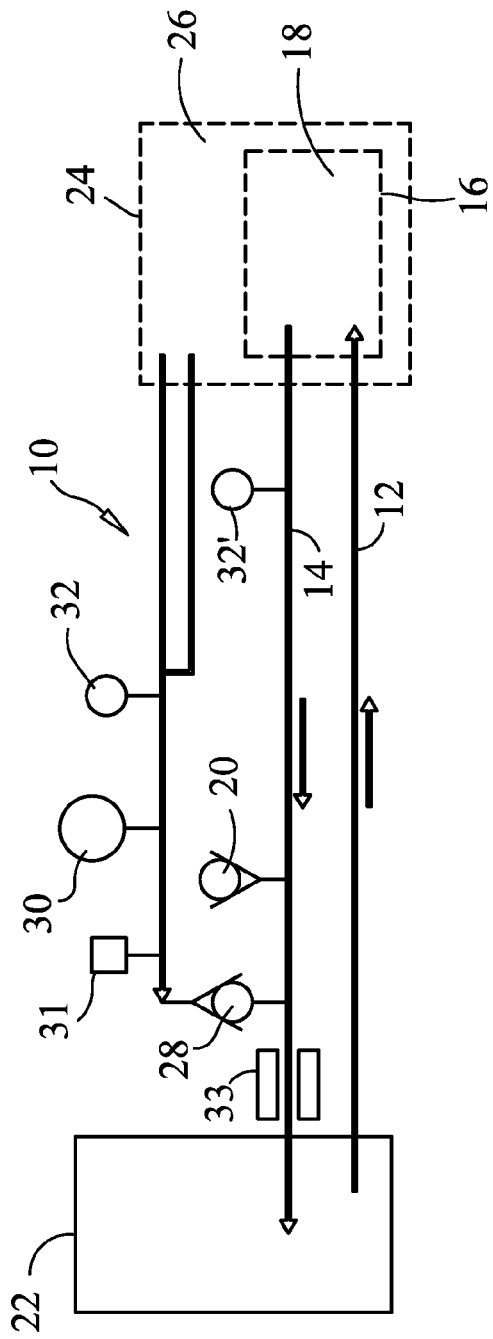
FIG. 1 illustrates a fluid control system for a medical device in accordance with the present invention.

Now referring to FIG. 1, the present invention advantageously provides a fluid control and leak detection system for a medical device 10. Specifically, a medical device 10 is provided having an elongate body with both a proximal end and a distal end, with the elongate body defining an intake lumen 12 and an exhaust lumen 14. A first pliable element 16 defining a cooling chamber 18 is disposed on the elongate body, and is in fluid communication with both the intake lumen 12 and the exhaust lumen 14. Although illustrated in FIG. 1 as being disposed at the distal end of the elongate body, the cooling chamber 18 may be located at any point along the elongate body of the medical device 10. Moreover, the cooling chamber 18 may be of any shape or orientation and is not limited to a circular or spherical shape.

The intake lumen 12 provides a conduit through which a liquid or gas may flow from a fluid source, such as a coolant reservoir, as the fluid moves toward the cooling chamber 18. Further, the exhaust lumen 14 provides a conduit for a liquid or gas to exit the cooling chamber 18 and flow towards a coolant receptacle, re-circulator, or the like. The exhaust lumen 14 may also have an exhaust valve 20 that releases excess pressure to an external environment if there is a kink or blockage along the length of the medical device 10.

In order to facilitate fluid flow, the intake lumen 12 may be coupled to a pressurized fluid source. Moreover, the exhaust lumen 14 may be coupled to a vacuum source in order to draw the fluid out of the medical device 10. Each of the coolant receptacle, re-circulator, pressurized fluid source and/or the vacuum source may be integrated into a single control console 22 or unit to which the medical device 10 is coupled.

The medical device 10 of the present invention further includes a second pliable element 24 at least partially enclosing the first pliable element 16, thereby defining a junction 26 between the first and second pliable elements. The second pliable element 24 provides a safeguard to prevent fluid from leaking out of the cooling chamber 18 and into surrounding tissue should the first pliable element 16, and therefore the cooling chamber 18, rupture or develop a leak. The junction 26 between the first and second pliable elements may be substantially under a vacuum, such that the first and second pliable elements are generally in contact with each other, with little or no open space between them.

A first check valve 28 is provided in fluid communication with the junction 26 between the first and second pliable element 16 and 24, respectively, with the first check valve 28 also being in fluid communication with the exhaust lumen 14. The first check valve 28 is a one way valve that prevents fluid from traveling from the exhaust lumen 14 into the junction 26 between the first and second pliable element 16 and 24, respectively, yet allows fluid, if any, to flow from the junction 26 between the first and second pliable element 16 and 24, respectively towards the exhaust lumen 14. The check valve may be such that the valve opens automatically in response to a pressure change in the junction 26.

In addition, a first pressure sensor 30 or other means for monitoring the conditions in the junction 26 may be provided in fluid communication with the junction 26 between the first and second pliable element 16 and 24, respectively. The first pressure sensor 30 can detect a pressure change in the junction 26, which would be indicative of a leak or other operational anomaly, which could then be used to trigger a shut-down of fluid supply through the intake lumen 12 or an evacuation sequence of the fluid in the medical device 10.

The medical device 10 can include a semiconductor element 31 in fluid communication with the junction 26. The semiconductor element 31 can calibrate the conditions under which the first pressure sensor 30 will trigger a shut-down by taking into account the operating pressure and temperature within a portion of the medical device, then setting the threshold level of the first pressure sensor 30 accordingly. The semiconductor device 31 can further include a pressure profile under which the first pressure sensor 30 can be triggered. For example, the pressure profile contained in the semiconductor chip could calibrate the first pressure sensor 30 to respond should the pressure in the junction 26 rise rapidly. However, in the event that the pressure in the junction 26 rises at a very slow rate, i.e., in the event of a pinhole leak or the like, then the first pressure sensor 30 can be calibrated not to respond. In either event, the semiconductor element 31 can include appropriate information concerning the rate at which pressure builds, the time lapse during such pressure increase, or the like, and calibrate the first pressure sensor 30 to act accordingly. The semiconductor element 31 also can communicate control signals such as temperature, threshold levels and other factors involved in calibrating the first pressure sensor 30 to the console 22.

In addition, the semiconductor element 31 can include an identification code which can be communicated to the console 22 in order to determine the past use history of the particular medical device 10 as well as the typical operating procedures applicable for the medical device 10. This identification code can be used to prevent re-use or misuse of the medical device 10.

Moreover, a leak detection element 32 may be included in fluid communication with the junction 26 to provide the ability to detect any ingress of blood or fluid into the junction 26, further indicating a leak or other structural compromise of the medical device 10. An additional leak detection element 32' may be included in fluid communication with the exhaust lumen 14. The leak detection element 32 can detect an ingress of fluid in the junction 26 by providing an impedance measurement, which would change upon the presence of a fluid within the junction. Moreover, leak detection element 32' can detect the ingress of blood or tissue fluid in the exhaust lumen from a similar impedance measurement, which would change due to the addition of tissue fluid or blood to the fluid circulating in the medical device 10. The leak detection elements 32 and 32' can have preconfigured values for normal operating conditions, thereby triggering a response should conditions exceed the preconfigured values.

As an additional safeguard, an infrared detection element 33 may be included adjacent to a length of the exhaust lumen 14. The infrared detection element 33 can monitor the optical characteristics of the fluid within the exhaust lumen 14, thereby providing the detection of blood or any opaque substance within the fluid flow of the exhaust lumen.

Figure 2:
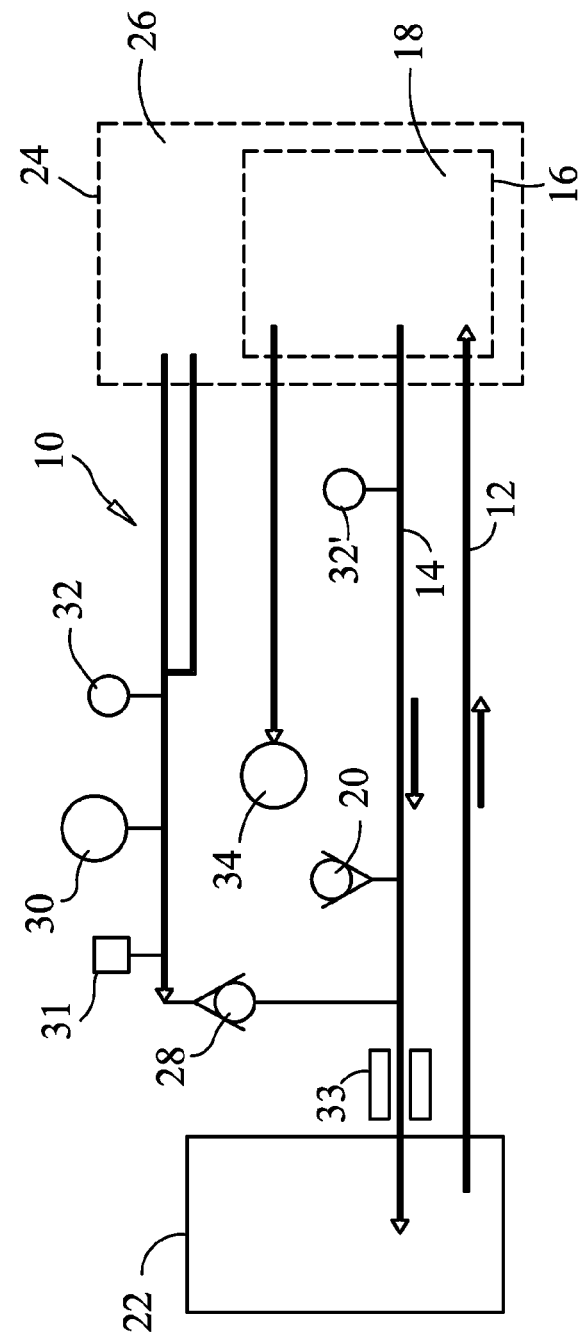
FIG. 2 shows an alternative fluid control system for a medical device in accordance with the present invention.

Now referring to FIG. 2, the medical device 10 can further include a second pressure sensor 34 in fluid communication with the cooling chamber 18. The second pressure sensor 34 can monitor the conditions within the cooling chamber 18, and could further trigger a shut-down or evacuation sequence once a particular condition or pressure level in the cooling chamber 18 has been reached or exceeded. The addition of the second pressure sensor 34 provides constant and continuous monitoring of fluid pressure in the cooling chamber 18, thereby providing the ability to discontinue fluid flow through the medical device 10 prior to a structural compromise or breach of the first pliable element 16 due to elevated pressure levels. Furthermore, the second pressure sensor 34 can operate as a pressure feedback loop, wherein the second pressure sensor 34 communicates pressure measurements of the fluid in the cooling chamber 18 to the console 22, and the console 22 can then modify the pressure of fluid being provided to the medical device 10.

Figure 3:
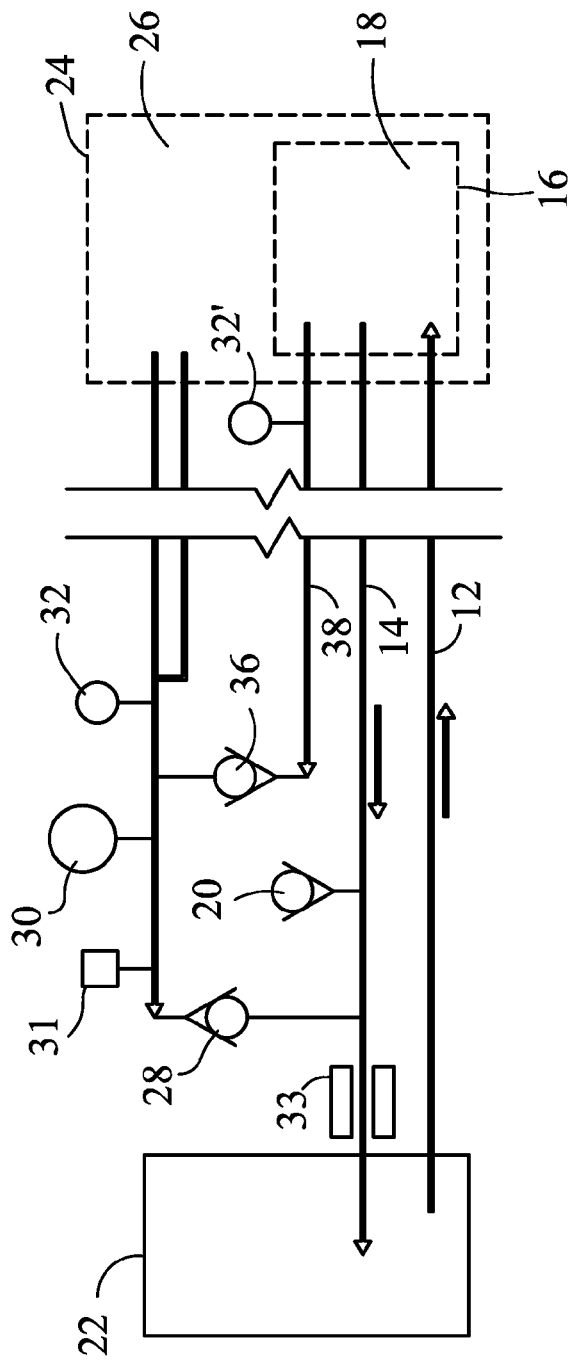
FIG. 3 depicts an additional alternative fluid control system for a medical device in accordance with the present invention.
Figure 4:
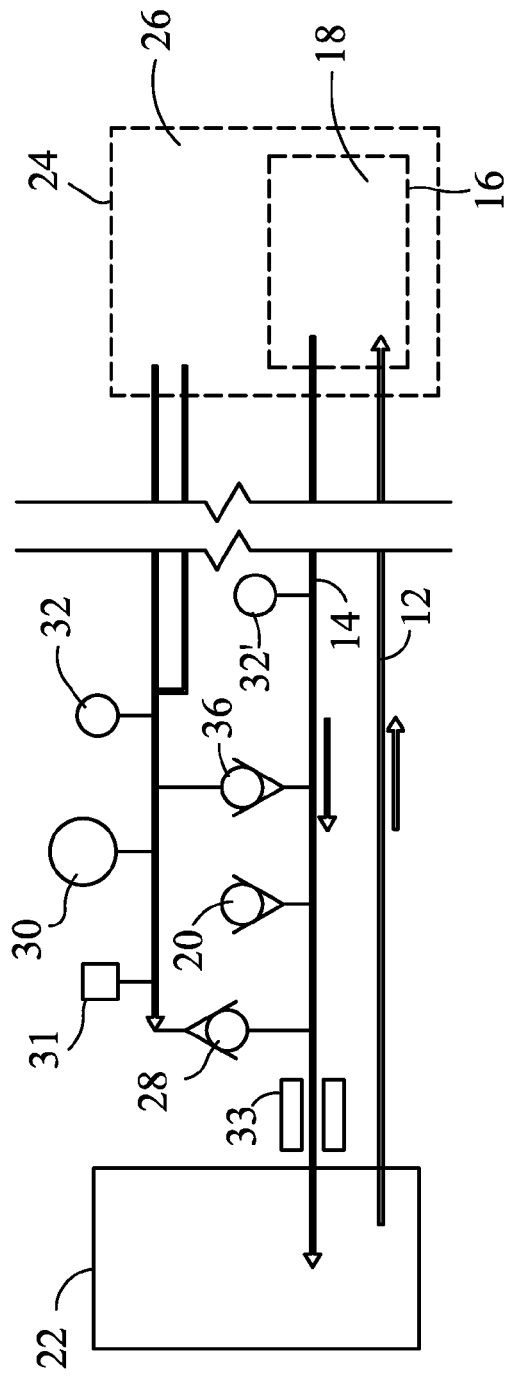
FIG. 4 shows yet another alternative fluid control system for a medical device in accordance with the present invention.

Although having the first and second pressure sensors provides monitoring of both the conditions in the junction 26 and in the cooling chamber 18, respectively, a second check valve 36 can be placed in fluid communication with the cooling chamber 18 while also being in fluid communication with the junction 26, as shown in FIGS. 3 and 4. The second check valve 36 is a one-way valve that would allow fluid to flow from the cooling chamber 18 into the junction 26 upon reaching a certain fluid pressure level within the cooling chamber 18, yet prevent fluid, if any, from flowing from the junction 26 into the cooling chamber 18. By employing the second check valve 36, the first pressure sensor 30 can be used to monitor and trigger a shut-down or evacuation sequence due to changes in pressure in either the junction 26 or the cooling chamber 18. For example, the second check valve 36 can be configured to open at a pressure level somewhat greater than the expected operating pressure level in the cooling chamber 18. As a result, if the pressure exceeds a predetermined safe operating level, the second check valve 36 is opened. Subsequently, fluid will flow into the junction 26 and the pressure in the junction 26 will change. The first pressure sensor 30 can detect the pressure change and shut down the operation of the medical device 10. The second check valve 36 can be in fluid communication with the cooling chamber 18 through an additional relief lumen 38, or may alternatively be directly connected to the exhaust lumen 14. Moreover, the second check valve 36 may be placed in fluid communication with the exhaust lumen along a length of the medical device where the general operating pressure is known, which would simplify preconfiguring the pressure level at which the check valve should open.

Figure 5:
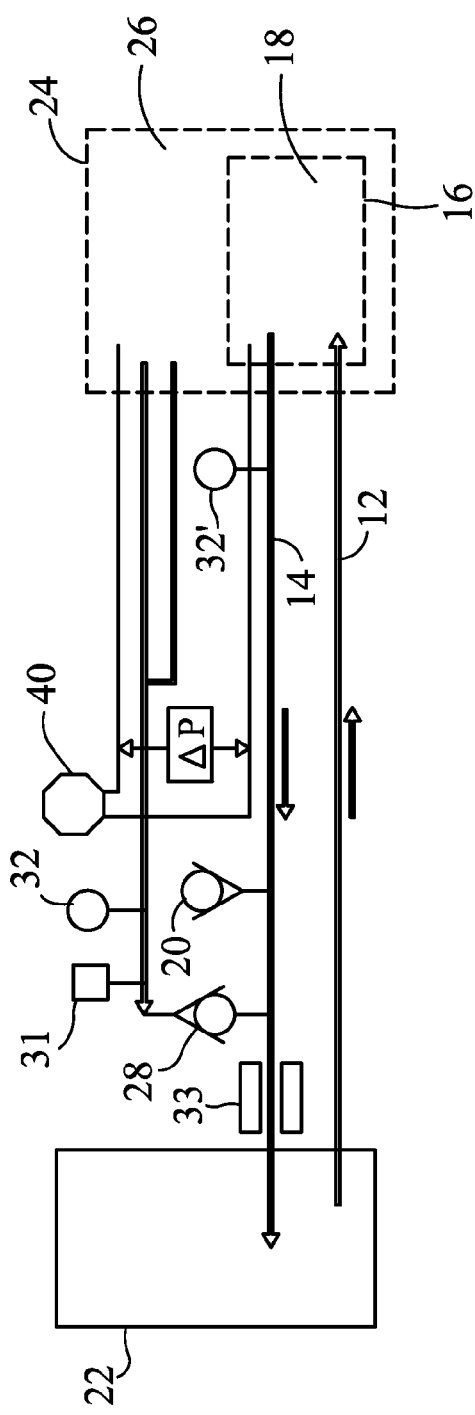
FIG. 5 illustrates an additional fluid control system in for a medical device in accordance with the present invention.

Now referring to FIG. 5, in an alternative embodiment, a pressure differential element 40 may be disposed on the medical device 10 in fluid communication with both the cooling chamber 18 as well as the junction 26 between the pliable elements. The pressure differential element 40 monitors the difference between the pressure in the junction 26 and the pressure in the cooling chamber 18. Should the difference in pressure fall outside a predetermined range, thereby indicating a leak or other operational anomaly, then a shut-down or evacuation procedure can be initiated. For example, if the first pliable element 16 remains intact, yet the cooling chamber 18 becomes increasingly pressurized due to a kink or blockage in the exhaust lumen 14, then the pressure difference between the first and second pliable elements will increase. If the first pliable element 16 develops a leak, allowing fluid to proceed into the junction 26, then the pressure difference will decrease. Additionally, if the first pliable element 16 remains intact yet the second pliable element 24 has a breach and blood or tissue fluid flows into the junction 26, then the pressure difference will decrease or increase, depending on the particular mode of operation the medical device is currently engaged in. The pressure differential element 40 can be preconfigured to respond should the pressure conditions fall outside a predetermined operating range for the medical device 10.

Figure 7:
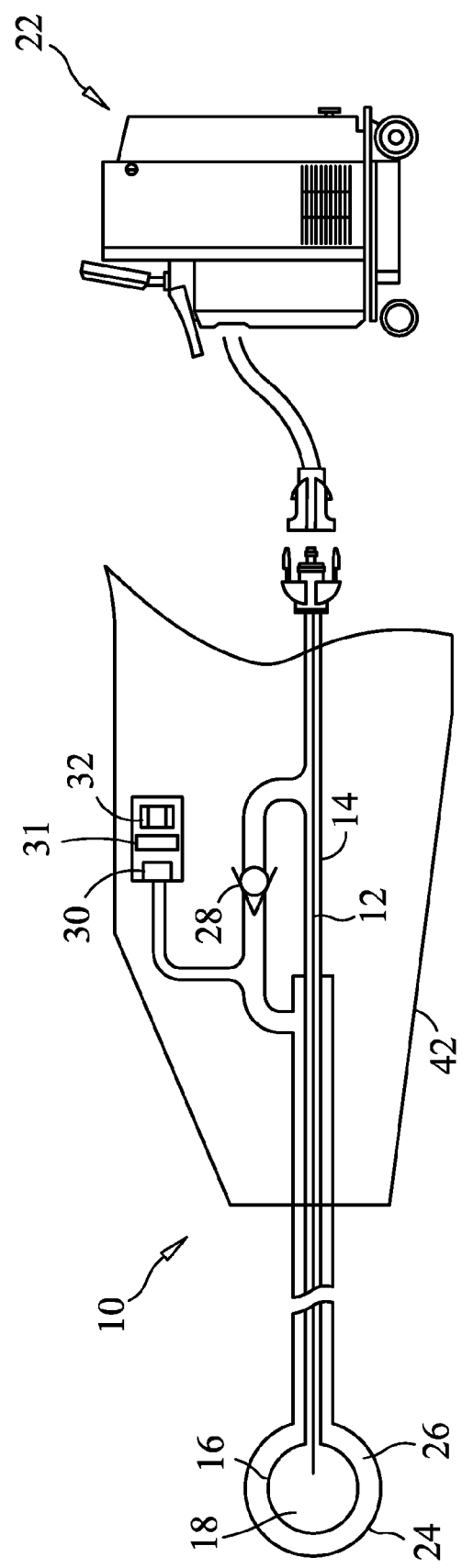
FIG. 7 shows an alternative medical device having a fluid control system in accordance with the present invention.
Figure 6:
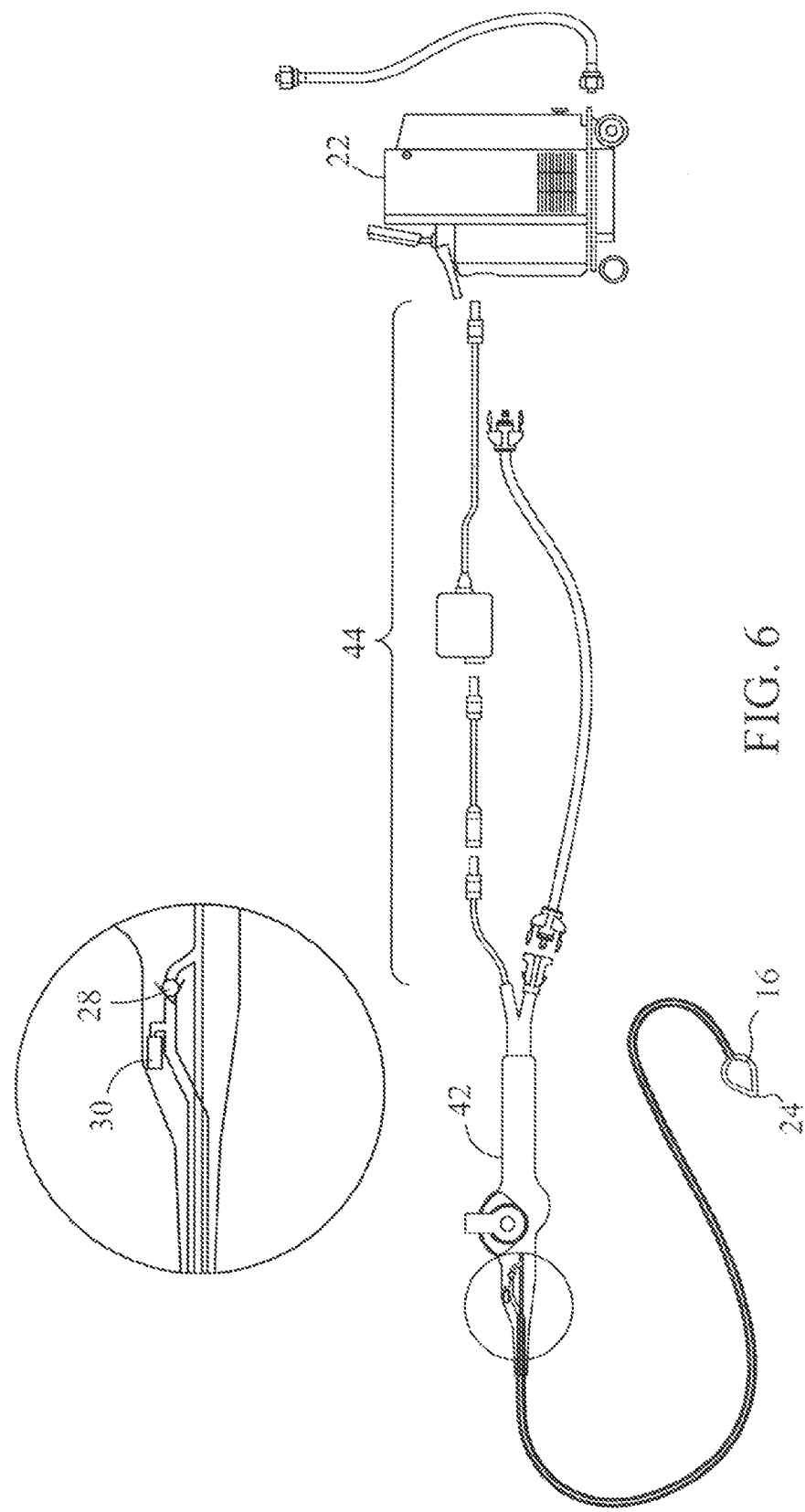
FIG. 6 depicts a medical device having a fluid control system in accordance with the present invention.

Of particular note, the location on the medical device 10 where the check valves, pressure sensors, or leak detection elements are disposed is not limited to the immediate vicinity of the cooling chamber 18. Particularly, as shown in FIGS. 6 and 7, the check valves, pressure sensors, or leak detection element may be located in a handle 42 of the medical device 10, in a medical accessory, or in the console 22 in order to reduce the number of components and thus the size of the portion of the medical device 10 which is inserted into a patient. Moreover, while the second pliable element 24 at least partially encloses the first pliable element 16, the second pliable element 24 may traverse a substantial portion of the elongate body of the medical device 10 in order to allow the placement of the check valves, pressure sensors, or leak detection element to be varied.

The present invention further provides for connection of the medical device 10 to the console 22. The console 22 can include the fluid circulation sources as described above, and may further be adapted to receive signals, electronic or otherwise, from any sensors included in the medical device 10. The connection between the medical device 10 and the console 22 may be achieved through an umbilical system 44 or the like, in order to provide connectivity to the multiple lumens as well as connectivity to the sensors. The console 22 can further include programming or software that provides a predetermined operational response when a particular level or event is detected by the sensors of the medical device 10. For example, should the pressure sensors detect a pressure exceeding the specified operational ranges, the console 22 may automatically cease providing pressurized fluid to the medical device 10, may initiate a fluid evacuation procedure to empty any fluid from the medical device 10, or may simply provide an audible alarm alerting the operator of the medical device 10.

In an exemplary operation of the medical device 10 of the present invention, a first fluid path is provided from the intake lumen 12 towards the cooling chamber 18, with the fluid proceeding out of the cooling chamber 18 defined by the first pliable element 16 and into the exhaust lumen 14. The fluid flow is maintained either by a pressurized fluid source in fluid communication with the intake lumen 12, a vacuum source in fluid communication with the exhaust lumen 14, or a combination of both. Employing either a pressurized fluid source or a vacuum, there is a lower fluid pressure in the exhaust lumen 14 than that of the intake lumen 12, which provides the movement of fluid through the first fluid path. At least partially surrounding the first pliable element 16 is the second pliable element 24, with the junction 26 formed therebetween substantially under a vacuum. As the first check valve 28 is provided in fluid communication with both the junction 26 between the first and second pliable element 16 and 24, respectively as well as the exhaust lumen 14, the fluid pressure in the exhaust lumen 14 is higher than that of the vacuum pressure in the junction 26. As a result, the check valve remains closed under normal operating conditions, preventing any fluid flow through the check valve.

However, in the event of a leak or rupture of either the first pliable element 16 or the second pliable element 24, fluid will flow into the junction 26 between the two pliable elements, thus eliminating the vacuum in the junction 26. As a result, if the pressure in the junction 26 exceeds that of the pressure in the exhaust lumen 14 downstream of the check valve, then the first check valve 28 will open. Subsequently, as the first check valve 28 is forced open due to the pressure change, a second fluid path results, which flows from the cooling chamber 18 into the junction 26 between the first and second pliable element 16 and 24, respectively, through the check valve, and into the exhaust lumen 14.

Whether or not the first check valve 28 is indeed forced opened, the pressure change in the junction 26 between the pliable elements will be detected by the first pressure sensor 30. This detected condition can trigger a response in the console 22, whereby a predetermined sequence of events can be initiated in the console 22, i.e., shut-down or evacuation of the medical device 10. The first pressure sensor 30 provides substantially instantaneous detection and notification of a leak, rupture, or other operating anomaly which falls outside of the safe operating ranges of fluid flow and pressure in the junction 26 of the medical device 10.

Should the medical device 10 include the second pressure sensor 34, an additional layer of safety and protection is ensured. In addition to the detection by the first sensor of pressure changes due to a breach of either the first or second pliable elements and the resulting pressure changes and fluid flow into the junction 26, the second pressure sensor 34 can trigger a response in the console 22 should the pressure in the cooling chamber 18 begin to rise towards unsafe operating ranges. The second pressure sensor 34 can then elicit a preventative shut-down or evacuation sequence by the console 22 prior to the occurrence of a breach of either the first or second pliable elements due to the rising pressure.

In an embodiment where the medical device 10 includes the pressure differential element 40, a rise or fall of the pressures within the junction 26 or cooling chamber 18, whether due to a breach of either pliable element or a blockage in the exhaust lumen 14, can be monitored. Such conditions which would then trigger a response in the console 22 upon exceeding normal operating ranges.

Alternatively, if the medical device 10 includes the second check valve 36, and the fluid pressure in the cooling chamber 18 or exhaust lumen 14 exceeds a predetermined safe operating range, the second check valve 36 will be forced to open, again providing a fluid path flowing from the cooling chamber 18 or exhaust lumen 14 and into the junction 26. The resulting pressure change and fluid flow in the junction 26 is detected by the first pressure sensor 30, which is then relayed to the console 22 for subsequent action. By configuring the second check valve 36 to open at a predetermined threshold level, should the pressure in the cooling chamber 18 rise beyond appropriate levels, the medical device 10 can be shut down by the console 22 prior to structural failure or breach of the pliable elements.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical device, comprising:
   an elongate body defining a first fluid path and a second fluid path, the elongate body being sized to be passed through vasculature;
   a pressure differential element in fluid communication with the first and second fluid paths; and
   a check valve directing one-way fluid flow from the second fluid path to the first fluid path.

2. The medical device according to claim 1, wherein the first fluid path includes an intake lumen and an exhaust lumen.

3. The medical device of claim 2, further comprising:
   a first pliable element defining a cooling chamber disposed at a point along the elongate body, the cooling chamber being in fluid communication with the intake lumen and the exhaust lumen; and
   a second pliable element at least partially enclosing the first pliable element, defining a junction between the first and second pliable element, the junction being in fluid communication with the second fluid path.

4. The medical device according to claim 3, further comprising a leak detection element in fluid communication with the junction.

5. The medical device according to claim 3, wherein the check valve allows one-way fluid flow from the junction between the first pliable element and second pliable element to the exhaust lumen.

6. The medical device according to claim 3, further comprising a semiconductor element in fluid communication with the junction.

7. The medical device according to claim 3, further comprising a leak detection element in fluid communication with the junction.

8. A medical device, comprising:
   an elongate body defining a first fluid path and a second fluid path, the elongate body being sized to be passed through vasculature, the first fluid path including an intake lumen and an exhaust lumen;
   a pressure differential element in fluid communication with the first and second fluid paths;
   a first pliable element defining a cooling chamber disposed at a point along the elongate body, the cooling chamber being in fluid communication with the intake lumen and the exhaust lumen;
   a second pliable element at least partially enclosing the first pliable element, defining a junction between the first pliable element and the second pliable element, the junction being in fluid communication with the second fluid path; and
   a check valve direction one-way fluid flow from the junction between the first pliable element and the second pliable element and the second pliable element to the exhaust lumen.

\* \* \* \* \*